United States Patent
Colvin, Jr.

[11] Patent Number: 5,917,605
[45] Date of Patent: Jun. 29, 1999

[54] FLUORESCENCE SENSING DEVICE

[76] Inventor: Arthur E. Colvin, Jr., 12321 Middlebrook Rd., Germantown, Md. 20874

[21] Appl. No.: 08/855,236

[22] Filed: May 13, 1997

[51] Int. Cl.[6] .................................................. G01N 21/25
[52] U.S. Cl. .................. 356/417; 422/82.07; 250/458.1; 436/172
[58] Field of Search ..................................... 356/417, 440, 356/416, 39, 410, 246, 436, 437, 317–318; 385/12, 13; 250/364, 365, 458.1, 459.1, 461.1, 461.2, 227.11–227.24; 128/633.01, 634; 436/172, 68, 163, 169, 178; 422/83, 68.1, 52, 91, 82.06, 82.07, 82.08

[56] References Cited

U.S. PATENT DOCUMENTS

| | | |
|---|---|---|
| 4,389,670 | 6/1983 | Davidson et al. . |
| 5,225,057 | 7/1993 | LeFebvre et al. . |
| 5,489,988 | 2/1996 | Ackley et al. . |
| 5,517,313 | 5/1996 | Colvin, Jr. . |
| 5,543,870 | 8/1996 | Blanchard . |
| 5,600,751 | 2/1997 | Peli . |

OTHER PUBLICATIONS

Colvin, Jr., A.E., et al., "A Novel Solid–State Oxygen Sensor," *Johns Hopkins APL Technical Digest*, vol. 17, No. 4, pp. 377–385 (1996).

*Primary Examiner*—K P Hantis
*Attorney, Agent, or Firm*—Rothwell, Figg, Ernst & Kurz

[57] ABSTRACT

A fluorescence sensing device for determining the presence or concentration of an analyte in a liquid or gaseous medium is constructed of a fiber optic plate comprising optical fibers having relatively small numerical apertures. The fiber optic plate is positioned on a photodetector and has a layer of analyte permeable fluorescent matrix or coated waveguide material on its top surface. The fluorescent matrix or waveguide coating contains indicator molecules whose fluorescence is affected by the local presence of analyte. A light source emits light into the fluorescent matrix in a direction generally parallel to the top surface of the fiber optic plate. Upon absorbing light from the light source, indicator molecules in the fluorescent matrix emit fluorescent light which is transmitted through the fiber optic plate to the photodetector.

19 Claims, 3 Drawing Sheets

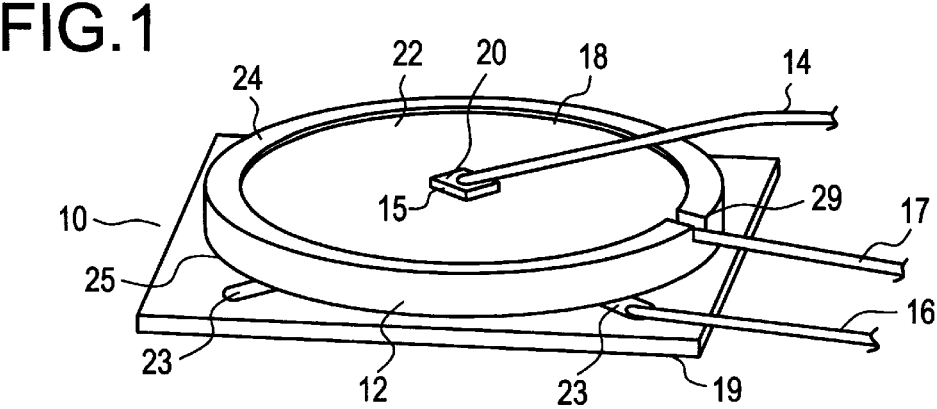
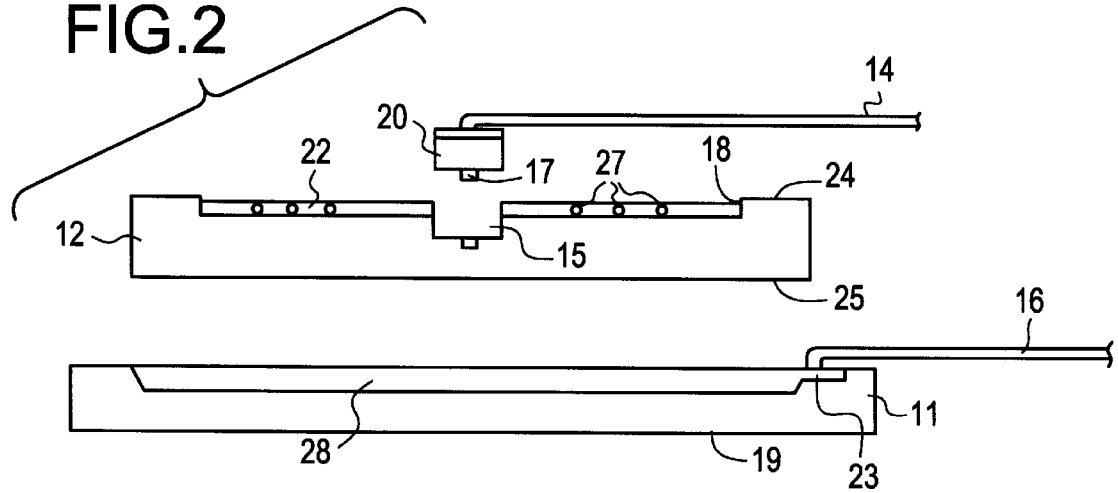
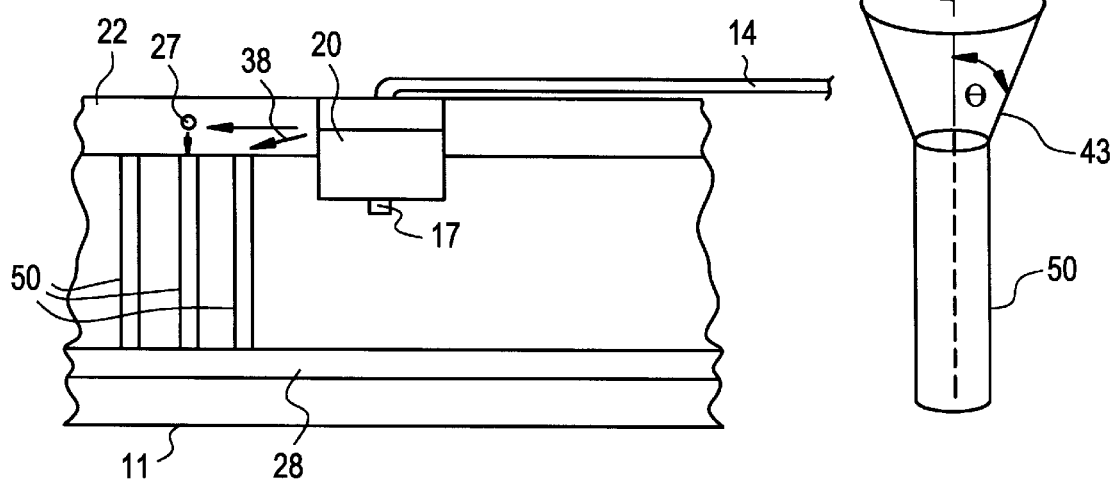

FLUORESCENCE SENSING DEVICE

BACKGROUND OF THE INVENTION

1. Field of Invention

This invention relates to an electro-optical sensing device for detecting the presence or concentration of an analyte in a liquid or gaseous medium. More particularly, the invention relates to a fluorescence sensing device which is characterized by a compact size, high sensitivity and high signal-to-noise ratios.

2. Background Art

U.S. Pat. No. 5,517,313, the disclosure of which is incorporated herein by reference, describes a fluorescence sensing device comprising a layered array of a fluorescent indicator molecule-containing matrix (hereafter, "fluorescent matrix"), a high-pass filter and a photodetector. In this device, a light source, preferably a light-emitting diode ("LED"), is located at least partially within the fluorescent matrix, such that incident light from the light source causes the indicator molecules to fluoresce. The high-pass filter allows emitted light to reach the photodetector, while filtering out scattered incident light from the light source.

The fluorescence of the indicator molecules employed in the device described in U.S. Pat. No. 5,517,313 is modulated, e.g., attenuated or enhanced by the local presence of the analyte. For example, the orange-red fluorescence of the complex, tris(4,7-diphenyl-1,10-phenanthroline)ruthenium(II) perchlorate is quenched by the local presence of oxygen. This complex can, therefore, advantageously be used as the indicator molecule of an oxygen sensor. Similarly, other indicator molecules whose fluorescence is affected by specific analytes are known.

In the sensor described in U.S. Pat. No. 5,517,313, the fluorescent matrix is permeable to the analyte. Thus, the analyte can diffuse into the fluorescent matrix from the surrounding test medium, thereby affecting the fluorescence emitted by the indicator molecules. The light source, fluorescent matrix, high-pass filter and photodetector are configured such that at least a portion of the fluorescence emitted by the indicator molecules impacts the photodetector, generating an electrical signal which is indicative of the concentration of the analyte in the surrounding medium.

While the sensing device described in U.S. Pat. No. 5,517,313 represents a marked improvement over prior art devices, there remains a need for sensors that are even more compact and which have superior sensing characteristics than those described therein. Thus, it is an object of the present invention to provide an improvement to the sensing devices described in the aforementioned patent.

BRIEF DESCRIPTION OF DRAWINGS

The invention will be illustrated by reference to the accompanying drawings in which:

FIG. 1 is a perspective view of one embodiment of a sensing device in accordance with the present invention;

FIG. 2 is a cross-sectional exploded view of the sensing device shown in FIG. 1;

FIG. 3 is an expanded cross-sectional view of the light source and surrounding structure of the sensing device shown in FIG. 1;

FIG. 5 is a schematic diagram of an optical fiber showing the cone of light acceptance;

SUMMARY OF THE INVENTION

Figure 4:
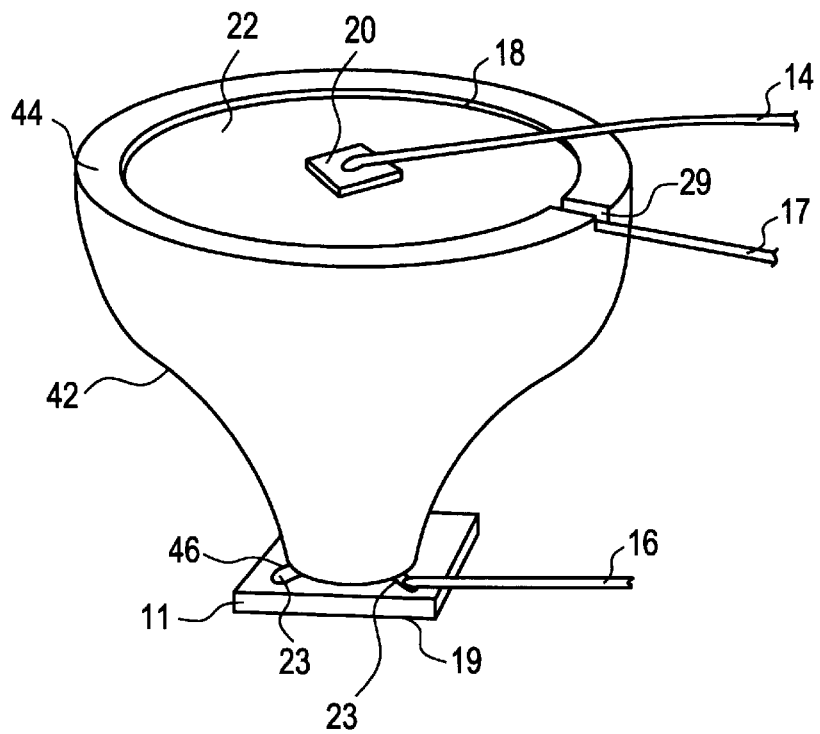
FIG. 4 is a cross-sectional view of an alternative embodiment of a sensing device in accordance with the present invention.

In accordance with the present invention, a fluorescence sensing device for determining the presence or concentration of an analyte in a liquid or gaseous medium comprises (a) a fiber optic plate having top and bottom surfaces, said plate comprising fibers having a relatively small numerical aperture;

(b) a layer of an analyte permeable fluorescent matrix positioned on the top surface of said fiber optic plate, said fluorescent matrix containing fluorescent indicator molecules whose fluorescence is modulated by the presence of analyte in said fluorescent matrix;

(c) a light source which emits light at a wavelength that excites fluorescence in the indicator molecules; at least a portion of the light from said light source being directed within the fluorescent matrix in directions generally parallel to the top surface of the fiber optic plate; and (d) a photodetector on the bottom surface of the fiber optic plate which generates an electrical signal responsive to fluorescent light emitted by said fluorescent indicator molecules.

DETAILED DESCRIPTION OF THE INVENTION

A fluorescent sensing device of this invention is shown in perspective view in FIG. 1. Sensor 10 comprises a fiber optic plate 12 having top and bottom surfaces 24 and 25, respectively. The fiber optic plate is a transverse section of a fiber optic bundle which contains fibers having a relatively low numerical aperture. The fiber optic bundle may be a coherent fiber optic bundle, i.e., one in which the relative positions of the ends of the fibers are maintained on both surfaces of the fiber optic plate. However, since transmission of a true image is not important in most applications the devices of this invention, it is usually not necessary that a coherent fiber optic bundle be used. The fibers within fiber optic plate 12 terminate at top surface 24 in an orientation substantially perpendicular to that surface. It is also preferred that the fibers be substantially perpendicular to the bottom surface 25.

Each fiber is made of a core of glass having a first refractive index and a cladding of glass having a second refractive index. Each fiber may also be clad in an opaque material to minimize interfiber transmission of light that is off axis at significant angles.

Fiber optic plate 12 effectively provides a zero thickness window. Light entering the fiber is transmitted through the fiber with very little transmission loss as a result of total internal reflection.

Fibers in fiber optic plate 12 are conventional, and advantageously range in diameter from about 5.5 to about 75 microns. When laser ablation is used to form the surface of the fiber optic plate 12, it is preferred that fibers having relatively small core and cladding dimensions be used. Such small fibers have been found to result in minimal surface imperfections resulting from the different rates of ablation of the core and cladding materials. Thus, when laser ablation is to be used, the fibers are preferably less than about 40 microns in diameter, most preferably less than about 25 microns in diameter.

The diameter and thickness of fiber optic plate 12 can vary substantially, depending upon the applications of the sensor. In typical constructions, the diameter of fiber optic plate 12 ranges from about 0.025 mm to about 15 mm, preferably from about 2.5 mm to about 13 mm, and its thickness ranges from about 1 to about 25 mm.

As discussed in greater detail below, one function of fiber optic plate 12 is to minimize the transmission of incident light generated by the light source used in the sensor. This function is accomplished by utilizing fibers that have a relatively small aperture. That is, the cone of light acceptance is narrow, such that only light impacting the ends of the fibers at small angles, relative to the axis of the fibers, is transmitted through the fiber. An optical fiber 50 having a longitudinal axis 41 and a light acceptance cone 43 is illustrated in FIG. 5. The half angle of acceptance, $\theta$, is the angle formed between axis 41 and the maximum angle of light acceptance. By proper selection of the core glass and the cladding material, manufacturers of optical fibers can control the cone of light acceptance of the fibers. Low aperture fiber optic bundles are well known. See e.g., U.S. Pat. No. 5,543,870.

The aperture of optical fibers may be expressed as the "numerical aperture." Numerical aperture is defined as the sine of the half angle of the acceptance cone, i.e., $\sin \theta$. Fiber optic plate 12 is composed of optical fibers having relatively low numerical apertures, preferably ranging from about 0 to about 0.7, most preferably from about 0.1 to about 0.5. Fiber optic plates suitable for use in this invention are commercially available, for example from Schott Fiber Optics, Southbridge, Massachusetts USA.

A layer of fluorescent matrix 22 is positioned on top surface 24 of fiber optic plate 12. The fluorescent matrix contains fluorescent indicator molecules 27 whose fluorescence is modulated by the local presence of analyte. Fluorescent matrix 22 is permeable to the analyte, so that analyte molecules can diffuse into and out of the matrix at a rate related to the concentration of the analyte in the surrounding liquid or gaseous medium. This matrix may consist of fluorescent indicator molecules 27 coated directly on the top surface 24 of fiber optic plate 12. Direct coating of the fluorescent indicator molecules may advantageously be achieved by the use of silane linkers. Preferably, fluorescent matrix 22 is a polymer matrix which can be cast into a sheet or film, deposited as a film through evaporation or polymerized from monomers or oligomers in situ. The polymer used in the matrix should be optically transmissive at the wavelengths of the excitation and emission of the indicator molecules.

A variety of polymers can be used for the preparation of fluorescent matrix 22. A polymer system that has been found useful for preparing an oxygen sensor employs silicone polymer RTV 118, available from General Electric Co., Pittsfield, Mass. USA. This polymer may be dissolved in a 1:1 to 1:6 petroleum ether/chloroform mixture. The fluorescent indicator ruthenium complex referred to above may be blended into the polymer solution at a concentration of from about 0.1 to 1 mM. The resulting mixture may then be applied to top surface 24 of fiber optic plate 12. Evaporation of the solvents results in the deposition of a fluorescent matrix film 22 on top surface 24.

In one embodiment, a recessed area 18 may be machined, e.g., by laser ablation or mechanical polishing and/or grinding, into top surface 24 of fiber optic plate 12. The recessed area 18 is filled with fluorescent matrix 22. This recessed area facilitates the deposition of a uniform thickness of fluorescent matrix 22.

Figure 6:
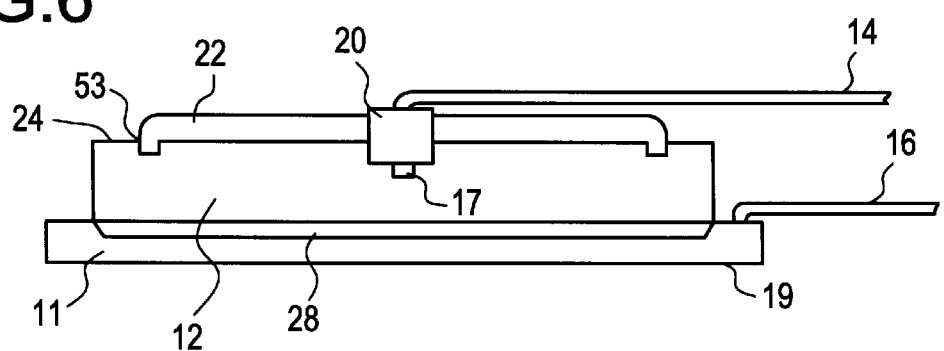
FIG. 6 is a cross-sectional view of another alternative embodiment of a sensing device in accordance with the present invention.

In an alternative embodiment, shown in FIG. 6, a moat 53 may be machined in top surface 24 of fiber optic plate 12. This moat serves to stop the spread of fluorescent matrix 22 when applied in the liquid state. By controlling the volume of liquid applied, e.g., with a micropipette or syringe, films of uniform depth can be produced.

Figure 7:
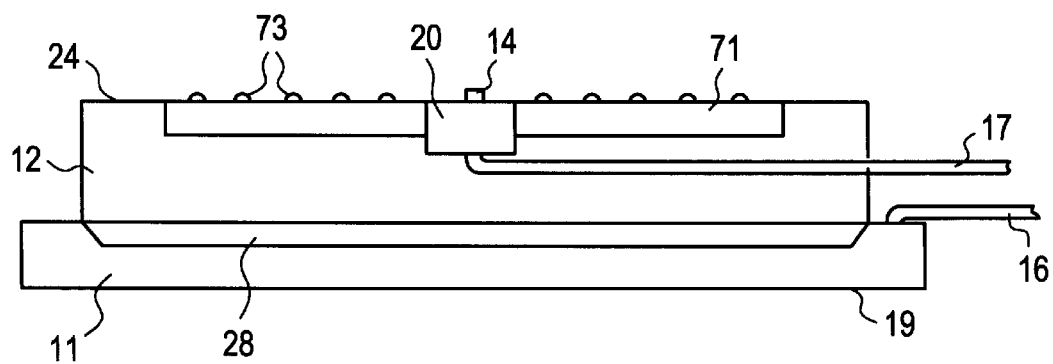
FIG. 7 is a cross-sectional view of an embodiment of the invention that employs an optical waveguide.

In an alternative embodiment illustrated in FIG. 7, a waveguide material 71 may be substituted for fluorescent matrix 22. In this embodiment, fluorescent indicator molecules 73 are positioned on the surface of waveguide material 71, such that they may be placed in contact with the liquid or gaseous test medium. Light emitted from LED 20 is largely contained within waveguide 71 through internal reflectance. Light reflected from the interface of the waveguide material and the surrounding medium passes far enough through the surface of the material to impact a fluorescent indicator molecule 73 deposited on the surface, thereby exciting analyte-concentration dependent fluorescence in the indicator molecule.

The waveguide material is prepared from a transparent material having a refractive index substantially higher than that of the liquid or gaseous medium with which it is in contact. A suitable material is, for example, clear acrylic polymer. When a waveguide material is used in place of the fluorescent matrix, it need not be permeable to the analyte, since the fluorescent indicator molecules are positioned on the surface of the waveguide material. Any of the physical embodiments described in connection with the fluorescent matrix material may also be employed with the waveguide embodiment.

Various light sources which emit light at appropriate excitation wavelengths and at least a portion of whose light can be directed through fluorescent matrix 22 in a direction generally parallel to top surface 24 of fiber optic plate 12 may be used in the practice of this invention.

The light source employed in the sensors of this invention is preferably a light-emitting P-N junction. Such devices are well known. Upon application of an electrical potential across the P-N junction, light is emitted in directions generally in the same plane as the junction. The P-N junction may be provided in a variety of configurations. For convenience it will be described hereafter as a conventional light-emitting diode ("LED") 20.

LED 20 is positioned such that it emits light within the layer of fluorescent matrix 22. As best illustrated in FIGS. 1 and 2, LED 20 is advantageously positioned in a pocket 15 in the upper surface of fiber optic plate 12. The LED is advantageously positioned such that its P-N junction is at about the center of the thickness of the fluorescent matrix 22.

Electrical leads 14 and 17 are attached to the top and bottom surfaces of LED 20, which in turn are connected to a suitable power supply (not shown). A groove 29 may be cut into fiber optic plate 12 to accommodate lower lead 17. The LED may be extremely small, typically having a dimension of about 200 to 300 microns on an edge.

Since, as illustrated in FIG. 3, the LED emits light from its edges, at least a portion of the light radiates outwardly from the LED in directions generally parallel to top surface 24 of fiber optic plate 12. Thus, the excitation light emitted by LED 20 passes through the fluorescent matrix 22 and may be absorbed by an indicator molecule 27, causing it to fluoresce.

Those skilled in the art will recognize that numerous other techniques may be used for creating the layer of fluorescent matrix 22. For example, the fluorescent matrix may be prepared in sheet form and suitably sized portions may be placed on top surface 24 of fiber optic plate 12 and secured with an optically transmissive adhesive. Alternatively, the construction illustrated in U.S. Pat. No. 5,517,313 may be employed, substituting fiber optic plate 12 for the high-pass filter employed in that device.

A portion of the light emitted from the indicator molecules is transmitted through fiber optic plate 12 and is detected by photodetector 11. The narrow-aperture optical fibers 50 will accept light emitted by fluorescent indicator molecules 27 that are within the cone of light acceptance of such fibers. On the other hand, light rays 38 emitted by LED 20 which impact the fibers at angles greater than the half angle of acceptance are not transmitted through fiber optic plate 12. Fiber optic plate 12 thus serves to transmit fluorescent light emitted by indicator molecules 27 with a high degree of efficiency, while reducing the amount of light from the LED 20 which reaches photodetector 11.

Photodetector 11 may be a conventional solid state photoelectric device resulting from the interface of two semiconductors.

Photodetector 11 advantageously has a photosensitive area 28 that corresponds in size and shape to bottom surface 25 of fiber optic plate 12. This photosensitive area may be created by well-known photomasking and infusion doping procedures. Electrical connections 23 may be positioned outside photosensitive area 28.

The photodetector produces an electrical signal in response to the amount of fluorescent light impacting it. This signal is transmitted by electrical lead 16 and bottom surface 19 to suitable amplification and measuring circuitry (not shown).

Fiber optic plate 12 and photodetector 11 may be mechanically joined with a suitable optical adhesive. Such adhesive provides a bond between the components, but does not absorb significant quantities of fluorescent light passing through the fiber optic plate. The refractive index of the optical adhesive is preferably substantially equal to or greater than that of the core of the optical fibers to facilitate transmission of light from the fibers through the adhesive. A suitable adhesive is available as Epotek™ No. 377 from Epoxy Technology, Bilerica, Mass. USA.

In the embodiment illustrated in FIG. 4, the fiber optic plate serves as a signal enhancer. In this embodiment, a tapered fiber optic bundle 42 is used as the fiber optic plate 12 shown in FIGS. 1–3. Tapered fiber optic bundles are well known. See, e.g., U.S. Pat. No. 5,600,751. As a consequence, light impacting top surface 44 is concentrated at bottom surface 46. Thus, the intensity of the fluorescent signal generated by fluorescent matrix 22 is enhanced at photodetector 11. Signal enhancements of factors of 2 or more, preferably 5 or more, most preferably 10 or more may be achieved in this manner.

The dimensions of tapered fiber optic bundle 42 may vary, depending on the applications. In a typical sensor employing this embodiment, the top surface 44 has a diameter ranging from about 10 to about 50 mm, and bottom surface 46 has a diameter ranging from about 0.25 to about 20 mm. As illustrated in the aforementioned U.S. Pat. No. 5,600,751, tapered fiber optic bundles may take on a variety of shapes. The fibers may be curved or skewed to fit a particular physical design of the sensor.

Figure 8:
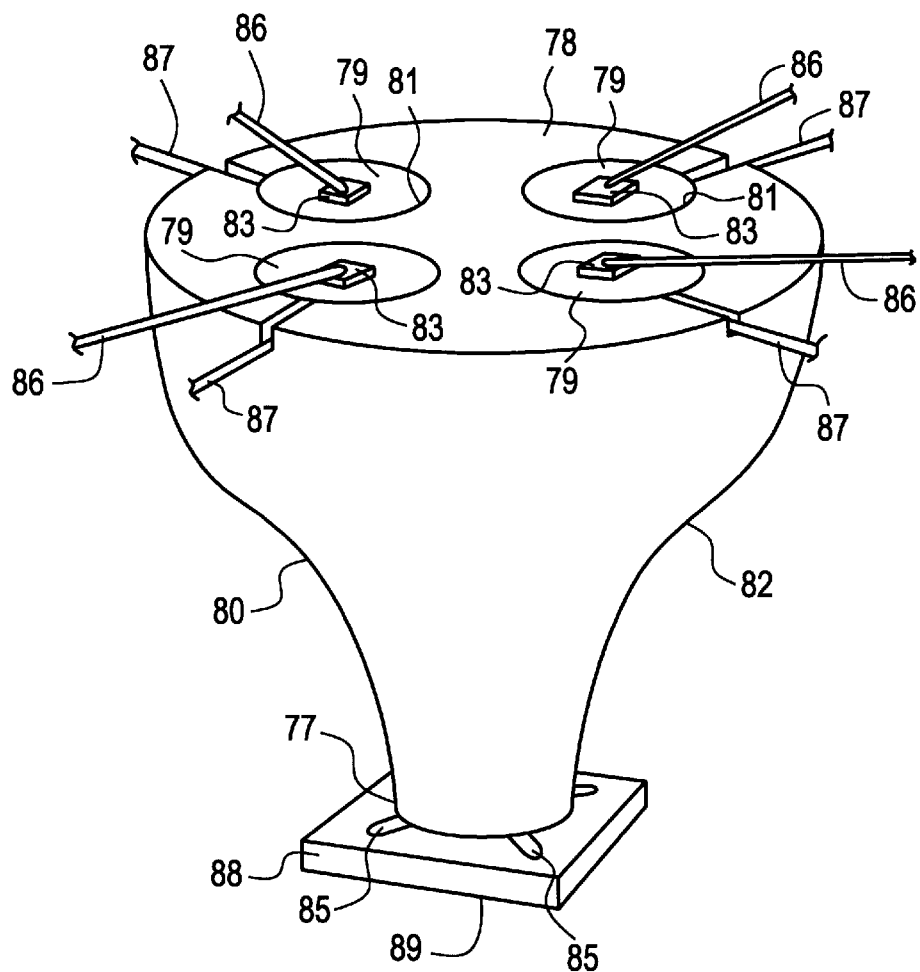
FIG. 8 is a perspective view of a multichannel embodiment of the sensing device of this invention.

The sensors of this invention may advantageously be configured for multichannel applications. Such a device is illustrated in FIG. 8. Sensor 80 comprises a tapered fiber optic bundle 82. A plurality of recessed areas 81 may be formed in the top surface 78 of fiber optic bundle 82. Each recessed area 81 contains fluorescent matrix or fluorescent indicator molecule-coated waveguide material 79, and each contains a light-emitting P-N junction 83, positioned as previously described. Electrical potential is applied to P-N junction 83 by means of leads 86 and 87.

Photodetector 88 is positioned on bottom surface 77 of fiber optic bundle 82. Photodetector 88 generates an electrical signal that is related to the intensity of the fluoescent light transmitted through fiber optic bundle 82.

Figure 9:
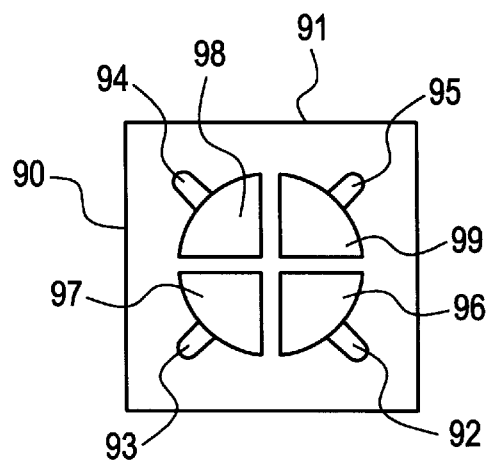
FIG. 9 is a top plan view of a photodetector for use in a multichannel embodiment of the invention.

Each of the recessed areas 81 may contain a different fluorescent indicator molecule that is responsive to a different analyte. Thus sensor 80 may be used to detect the presence or concentration of multiple analytes simultaneously. Photodetector 88 may have a single photosensitive area, in which case, each P-N junction 83 may be illuminated sequentially and the signal generated by photodetector 88 is measured in phase with each sequential illumination. Alternatively, a photodetector such as that illustrated in FIG. 9 may be employed. In that embodiment, separate photosensitive areas 96, 97, 98 and 99 are created by a photomasking or laser etching technique. These areas receive fluorescent light separately from each of the recessed areas 81 and the electrical signal is transmitted through electrical contacts 92, 93, 94 and 95 and bottom surface 91 of photodetector 90. When a separate channel photodetector such as that illustrated in FIG. 9 is used, fiber optic bundle 82 is preferably a coherent fiber optic bundle.

The structure of these devices permits the use of thin films of the fluorescent matrix. The thickness of the film advantageously ranges from about 500 Å to about 200 microns, preferably from about 10 to about 100 microns, most preferably from about 10 to about 20 microns.

The thinness of the film of fluorescent matrix 22 or the surface coating on waveguide 71 and the use of an edge-emitting P-N junction embedded in film 22 or waveguide 71 provides unique and advantageous characteristics to the devices of this invention. The response times of the device are primarily affected by the rate at which analyte can diffuse into and out of the indicator molecule-containing film. The films employed in the present devices have large surface areas and shallow depths. Therefore, analyte can diffuse to the site of an indicator molecule very quickly.

On the other hand, the optical signal available from the fluorescent indicator molecules is affected by the concentration of such molecules that can be placed in the path of excitation light. Since the excitation light passes transversely through film 22 or waveguide 71 from LED 20, optical efficiency is maximized.

Thus, it can be seen that the dimension responsible for optical absorption and the subsequent fluorescence is decoupled from the dimension in which the analyte of interest must diffuse into the indicator molecule-containing material. Optical absorbance is defined by Beer's law, while the rate of diffusion is defined by Fick's law. Chang, *Physical Chemistry*, pp. 64 and 147, McMillan, New York (1977). The decoupling of these two phenomena produces a device having very fast response times while maintaining a high signal-to-noise ratio.

The use of a fiber optic plate or tapered fiber optic bundle in the sensors of this invention serves to minimize the amount of excitation light reaching the photodetector, thus minimizing noise. The tapered fiber optic bundle embodiments have the added advantage of concentrating the fluorescent signal to increase the flux density, thus minimizing the need for concentration of the sample. If desired, noise may be further reduced by placing a cutoff filter either on the bottom surface or the top surface of the fiber optic plate or tapered fiber optic bundle. A preferred filter is a thin-film, dichroic $SiO_2/TiO_2$ electron-beam deposited filter such as those available from Optical Coating Laboratories, Inc., Santa Rosa, Calif. USA and described, for example, in U.S. Pat. No. 5,200,855, incorporated herein by reference. The filter is selected so as to transmit light emitted by the fluorescent indicator molecules while filtering out light emitted by the light source as well as a substantial portion of ambient light.

The fluorescence sensors of this invention may be used for measuring the presence or concentration of an analyte in a liquid or gaseous medium. When used in a liquid or hostile environment, the sensor and associated electrical components may be encapsulated in an inert resin material, such as an epoxy resin, leaving only the indicator molecule-containing film 22 or coated waveguide 71 exposed to the test medium. The sensors of this invention have a wide range of applications in industrial, medical and environmental fields. Examples of such applications are described in U.S. Pat. No. 5,517,313. A fluorescence sensor suitable for oxygen sensing is described by Colvin et al., *Johns Hopkins APL Technical Digest,* 17(4), 377–385 (1996), which is incorporated herein by reference.

The fluorescence sensors of this invention have been described in connection with certain preferred embodiments. Those skilled in the art will recognize that modifications and improvements may be made without departing from the spirit and scope of the invention as defined by the appended claims.

What is claimed is:

1. A fluorescence sensing device for determining the presence or concentration of an analyte in a liquid or gaseous medium comprising
   (a) a fiber optic plate having top and bottom surfaces, said plate comprising fibers having a relatively small numerical aperture, said fibers extending between said top and bottom surfaces of said plate;
   (b) a layer of an analyte permeable fluorescent matrix positioned on the top surface of said fiber optic plate, said fluorescent matrix containing fluorescent indicator molecules whose fluorescence is modulated by the presence of analyte in said fluorescent matrix;
   (c) a light source which emits light at a wavelength that excites fluorescence in the indicator molecules; at least a portion of the light from said light source being directed within the fluorescent matrix in directions generally parallel to the top surface of the fiber optic plate; and
   (d) a photodetector on the bottom surface of the fiber optic plate which generates an electrical signal responsive to fluorescent light emitted by said fluorescent indicator molecules and transmitted by said fibers through said fiber optic plate.

2. The fluorescence sensing device of claim 1, wherein the numerical apertures of the optical fibers in said fiber optic plate range from about 0 to about 0.7.

3. The fluorescence sensing device of claim 1, wherein the numerical apertures of the optical fibers in said fiber optic plate range from about 0.1 to about 0.5.

4. The fluorescence sensing device of claim 1, wherein the light source is a light-emitting P-N junction.

5. The fluorescence sensing device of claim 4, wherein the light source is a light-emitting diode ("LED").

6. The fluorescence sensing device of claim 4, wherein the light-emitting P-N junction is positioned at least partially within the fluorescent matrix.

7. The fluorescence sensing device of claim 1, wherein the fluorescent matrix comprises fluorescent indicator molecules dispersed in a polymer which transmits light at the wavelengths of excitation and emission of the fluorescent indicator molecules.

8. The fluorescence sensing device of claim 1, wherein the fiber optic plate is a tapered fiber optic bundle.

9. The fluorescence sensing device of claim 8, wherein the tapered fiber optic bundle concentrates the fluorescent light emitted by the fluorescent matrix by a factor of at least 2 at the photodetector.

10. The fluorescence sensing device of claim 1 or 8, wherein the fluorescent matrix has a depth of from about 500 Å to about 200 microns.

11. The fluorescence sensing device of claim 10, wherein the fluorescent matrix has a depth of from about 10 microns to about 100 microns.

12. The fluorescence sensing device of claim 1 or 8, wherein the top surface of the fiber optic plate has a recessed area having a depth and diameter sufficient to contain the layer of fluorescent matrix.

13. The fluorescence sensing device of claim 1 or 8, wherein the light source is positioned in a pocket in the top surface of the fiber optic plate, such that the P-N junction is positioned at about the center of the thickness of the fluorescent matrix.

14. The fluorescence sensing device of claim 1 or 8, wherein a moat is cut into the top surface of the fiber optic plate, surrounding the light source, and serves to stop the spread of the fluorescent matrix when it is applied in liquid form.

15. The fluorescence sensing device of claim 1 or 8, wherein the indicator molecule is the complex, tris(4,7-diphenyl-1,10-phenanthroline)ruthenium(II) perchlorate, and the fluorescence sensing device is an oxygen sensing device.

16. The fluorescent sensing device of claim 1 or 8 which further comprises an optical cutoff filter on the top surface or the bottom surface of the fiber optic plate, said optical cutoff filter having a relatively low absorbance for fluorescent light emitted by the fluorescent indicator molecules and having a relatively high absorbance for light emitted by said light source.

17. The fluorescence sensing device of claim 1 or 8 which comprises a plurality of discrete zones of fluorescent matrix positioned on the top surface of said fiber optic plate, each of said zones containing a fluorescent indicator molecule that is responsive to a different analyte.

18. The fluorescence sensing device of claim 17 wherein the photodetector comprises discrete photosensitive areas corresponding to each of the discrete zones of fluorescent matrix.

19. A fluorescence sensing device for determining the presence or concentration of an analyte in a liquid or gaseous medium comprising
   (a) a fiber optic plate having top and bottom surfaces, said plate comprising fibers having a relatively small numerical aperture, said fibers extending between said top and bottom surfaces of said plate;

(b) a layer of waveguide material on the top surface of said fiber optic plate, said waveguide material having on the surface thereof fluorescent indicator molecules whose fluorescence is modulated by the presence of analyte;

(c) a light source which emits light at a wavelength that excites fluorescence in the indicator molecules; at least a portion of the light from said light source being directed within the waveguide, such that it is largely contained within the waveguide and excites fluorescence in the indicator molecules on the surface of the waveguide; and (d) a photodetector on the bottom surface of the fiber optic plate which generates an electrical signal responsive to fluorescent light emitted by said fluorescent indicator molecules and transmitted by said fibers through said fiber optic plate.

\* \* \* \* \*